(12) United States Patent
Sheiman

(10) Patent No.: US 6,379,616 B1
(45) Date of Patent: Apr. 30, 2002

(54) STERILIZATION APPARATUS

(75) Inventor: Vladimir Lvovich Sheiman, Bondi Junction (AU)

(73) Assignee: Sheiman Ultrasonic Research (AU)

( * ) Notice: Subject to any disclaimer, the term of this patent is extended or adjusted under 35 U.S.C. 154(b) by 0 days.

(21) Appl. No.: 09/622,616

(22) PCT Filed: Feb. 17, 1999

(86) PCT No.: PCT/AU99/00089

§ 371 Date: Oct. 18, 2000

§ 102(e) Date: Oct. 18, 2000

(87) PCT Pub. No.: WO99/42145

PCT Pub. Date: Aug. 26, 1999

(30) Foreign Application Priority Data

Feb. 19, 1998 (AU) .............................. PP 1897

(51) Int. Cl.[7] ................................ A61L 9/00
(52) U.S. Cl. ..................... 422/31; 422/20; 422/24; 422/27; 422/128; 422/292; 422/306
(58) Field of Search ..................... 422/20, 24, 27, 422/128, 292, 306

(56) References Cited

U.S. PATENT DOCUMENTS

| | | | |
|---|---|---|---|
| 4,366,125 A | * 12/1982 | Kodera et al. | 422/20 |
| 4,424,188 A | * 1/1984 | DiGeronimo | 422/20 |
| 4,797,255 A | * 1/1989 | Hatanaka et al. | 422/20 |

FOREIGN PATENT DOCUMENTS

| | | |
|---|---|---|
| DE | 3840911 C1 | * 12/1988 |
| EP | 0 475 505 A1 | 3/1992 |

OTHER PUBLICATIONS

Derwent Abstract Accession No. 97–239592/22, Class D22, JP 09075432–A (EWA YG) Mar. 25, 1997—Abstract.
Derwent Abstract Accession No. 93–043359/05, Class S03, SU 1717054 A (Martynyuk) Mar. 7, 1992—Abstract.

* cited by examiner

*Primary Examiner*—Robert J. Warden, Sr.
*Assistant Examiner*—Imad Soubra
(74) *Attorney, Agent, or Firm*—Larson & Taylor, PLC

(57) ABSTRACT

A sterilization apparatus designed to receive an article requiring sterilization in which the apparatus comprises an aerosol generator operatively coupled to a sterilization chamber. The aerosol generator includes an ultrasonic transducer which is electrically coupled to an ultrasound generator. The sterilization apparatus also includes a tube which passes vertically through an apex of a partition ceiling formed in a nebulization chamber of the aerosol generator. The sterilization chamber includes a sterilization container which houses the article to be sterilized. The container includes an aerosol inlet and an aerosol outlet in communication with an expansion cavity and nebulization cavity of the nebulization chamber via an aerosol inlet conduit and an aerosol outlet conduit respectively. The sterilizing agent is nebulized via the transducer and recirculated through the sterilization chamber. Condensation of the aerosol is promoted within the sterilization chamber by another ultrasonic transducer or by heating of the aerosol via a heater.

14 Claims, 4 Drawing Sheets

STERILIZATION APPARATUS

The present invention relates generally to a sterilisation apparatus and a method of sterilisation and relates particularly, though not exclusively, to sterilisation involving ultrasonic nebulisation of a sterilising agent such as hydrogen peroxide.

It is recognised that the sterilisation of equipment can be achieved by exposing the equipment to an ultrasonically nebulised sterilising agent such as hydrogen peroxide. The sterilising agent is provided as an aerosol which effectively penetrates crevices, pores and other portions of the equipment which otherwise are not accessible by sterilizing agent in a liquid form.

Several US patents including U.S. Pat. No. 4,424,189 (Hick), U.S. Pat. No. 4,797,255 (Hatanaka et al), and U.S. Pat. No. 4,512,951 (Koubek) disclose the heating of a sterilising agent to effect evaporation of the sterilising agent which in its gaseous form is then contacted with the equipment to be sterilised. Although the gaseous sterilising agent is effective in penetrating the equipment the apparatus covered by these patents have the following drawbacks:
i) the apparatus is generally complicated in construction;
ii) the apparatus must be formed of materials resistant to the relatively high temperatures at which it is operated; and
iii) the choice of sterilising agents is restricted by the relatively high operating temperature.

Other US patents including U.S. Pat. No. 4,680,163 (Blidschun et al) and U.S. Pat. No. 4,366,125 (Kodera) describe ultrasonic nebulisation of a sterilising agent at ambient temperature. In these examples of the prior art an aerosol of the sterilising agent may condense on the equipment for effective sterilisation in the liquid form. However, the sterilising agent within the aerosol is of a low concentration as it is diluted with a carrier gas and/or the flow of the carrier gas and the aerosol is intermittent.

An intention of the present invention is to provide a sterilisation apparatus and a method of sterilisation that in operation are relatively effective.

According to one aspect of the present invention there is provided a sterilisation apparatus comprising:
an aerosol generator being adapted to generate an aerosol of a sterilising agent; and
a sterilisation chamber operatively coupled to the aerosol generator so as to receive a recirculatory flow of the aerosol, the sterilisation chamber being designed to receive an article requiring sterilisation whereby in operation the recirculatory flow of the aerosol through the sterilisation chamber is effective in sterilising the article.

According to another aspect of the present invention there is provided a sterilisation chamber being adapted to receive an article requiring sterilisation, the sterilisation chamber including an inlet and an outlet being configured to receive a recirculatory flow of an aerosol of a sterilising agent whereby in operation the recirculatory flow of the aerosol through the sterilisation chamber is effective in sterilising the article.

Generally the aerosol generator includes an ultrasonic transducer operatively coupled to or forming part of a reservoir which is adapted to contain the sterilising agent.

Preferably the sterilisation apparatus further comprises a tube positioned above the reservoir, the ultrasonic transducer being effective in producing a fountain of the sterilising agent into an inlet of the tube where the aerosol is produced.

It is understood that the aerosol is produced from a lower part of the fountain and the kinetic energy of the fountain within the tube increases the static pressure of the aerosol within the tube thereby inducing a pressure drop across the tube which alone serves to propel the aerosol.

Typically an outlet of the tube is coupled to or defines the inlet of the sterilisation chamber. More typically the outlet of the sterilisation chamber is coupled to or defines an air inlet, the aerosol being propelled through the tube under the assistance of air being drawn through the air inlet.

Preferably the apparatus further comprises means for effecting condensation of the aerosol within or on the article. Typically said means includes one or more of the following contrivances:
i) a heating element operatively coupled to the inlet of the sterilisation chamber;
ii) an ultrasonic transducer operatively coupled to the sterilisation chamber; and/or
iii) a device for increasing the pressure of aerosol within the sterilisation chamber.

Typically the apparatus also comprises means for rinsing and/or drying the condensed aerosol within or on the sterilisation chamber together with the article. Generally said rinsing and/or drying means is of a conventional construction.

Typically the aerosol generator and/or the sterilisation chamber are of a disposable design.

According to a further aspect of the present invention there is provided a method of sterilisation comprising the steps of:
providing a sterilisation apparatus including an aerosol generator and a sterilisation chamber operatively coupled to each other;
locating an article requiring sterilisation in the sterilisation chamber; and
providing a recirculatory flow of an aerosol of a sterilising agent through the sterilisation chamber whereby in operation the recirculatory flow of the aerosol through the sterilisation chamber is effective in sterilising the article.

Preferably the method of sterilisation further comprises the step of condensing the aerosol within or on the article. More preferably the method additionally includes the step of rinsing and drying the aerosol having been condensed within or on the article.

Generally the sterilising agent includes hydrogen peroxide or a derivative thereof.

According to yet another aspect of the present invention there is provided a switching device being designed to activate upon detection of a low level of liquid within a reservoir, the switching device comprising a cavitation signal detector operatively coupled to an ultrasound generator which is electrically coupled to an ultrasonic transducer located adjacent or defining the reservoir, the cavitation signal detector being configured to deactivate the ultrasound generator upon detection up to a threshold level of cavitation wherein there is sufficient liquid within the reservoir.

Preferably the switching device also comprises a filter electrically coupled to and located "upstream" of the cavitation signal detector, the filter being designed to filter all or part of the cavitation signal whereby said filtered portion only passes to the cavitation signal detector.

Typically the switching device also includes a blocking signal generator electrically coupled to a delay line which together operatively cooperate with the switching device to deactivate it when there is no cavitation.

Sterilisation is to be understood as including higher level disinfection.

In order to achieve a better understanding of the nature of the present invention a preferred embodiment of a sterilisation apparatus, a method of sterilisation and a switching device will now be described in some detail, by way of example only, with reference to the accompanying drawings in which.

Figure 1:
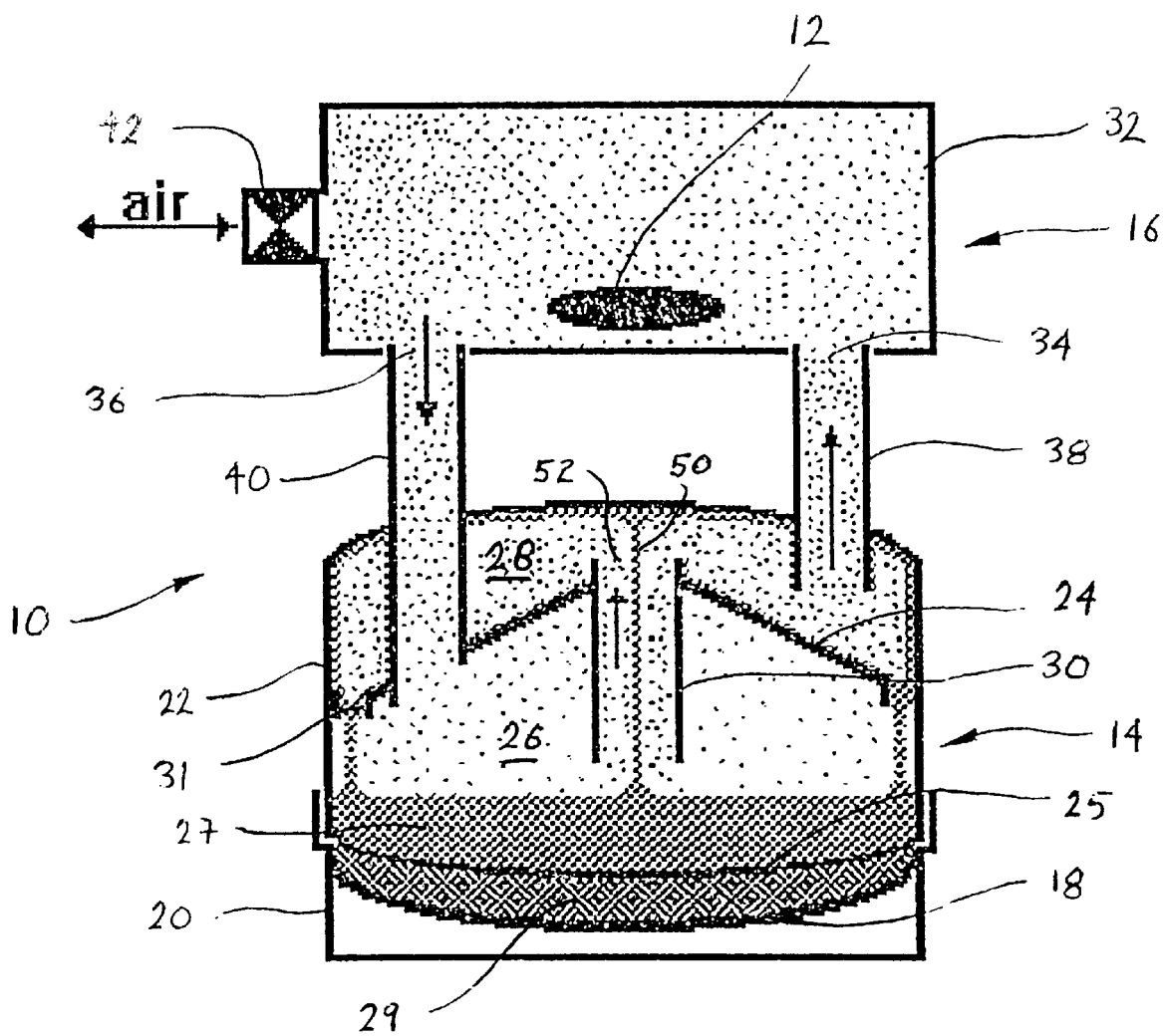
FIG. 1 is a schematic sectional view of one embodiment of a sterilisation apparatus.
Figure 2:
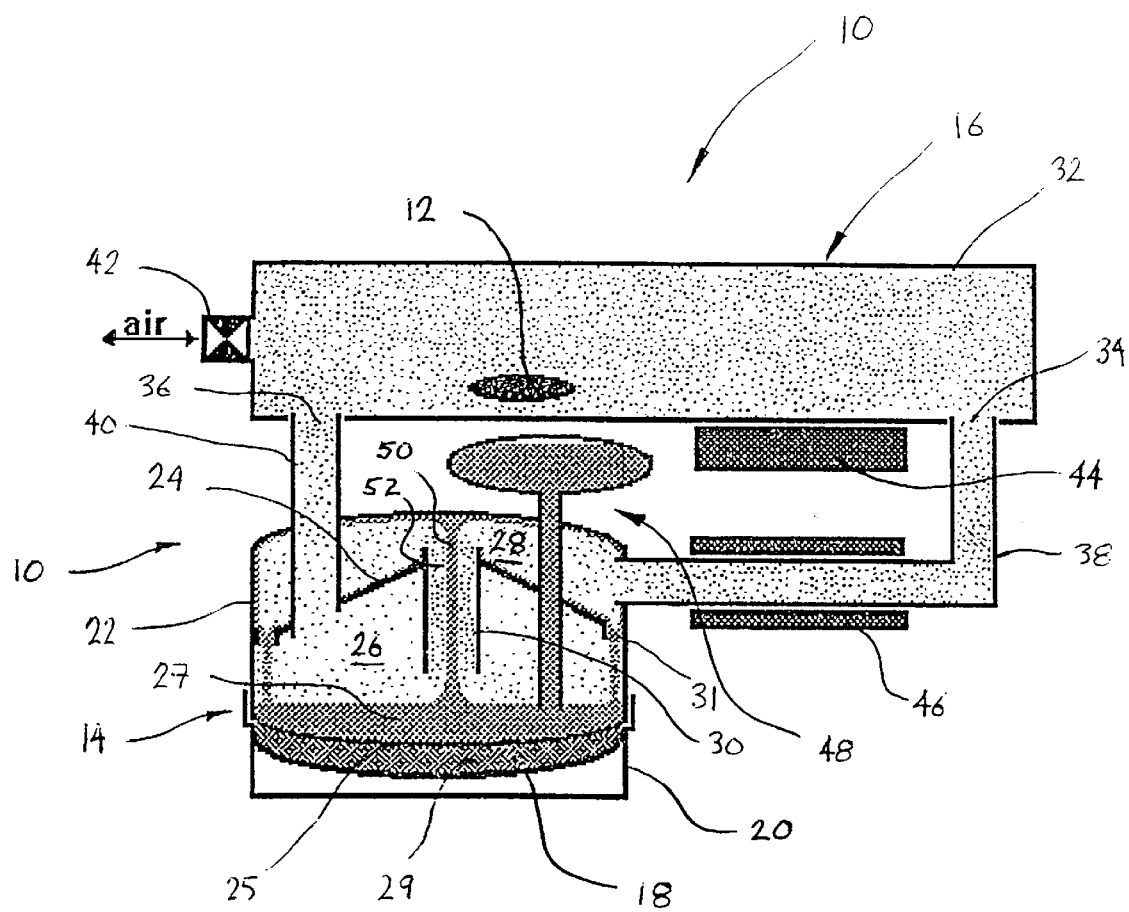
FIG. 2 is a schematic sectional view of another embodiment of a sterilisation apparatus.
Figure 3:
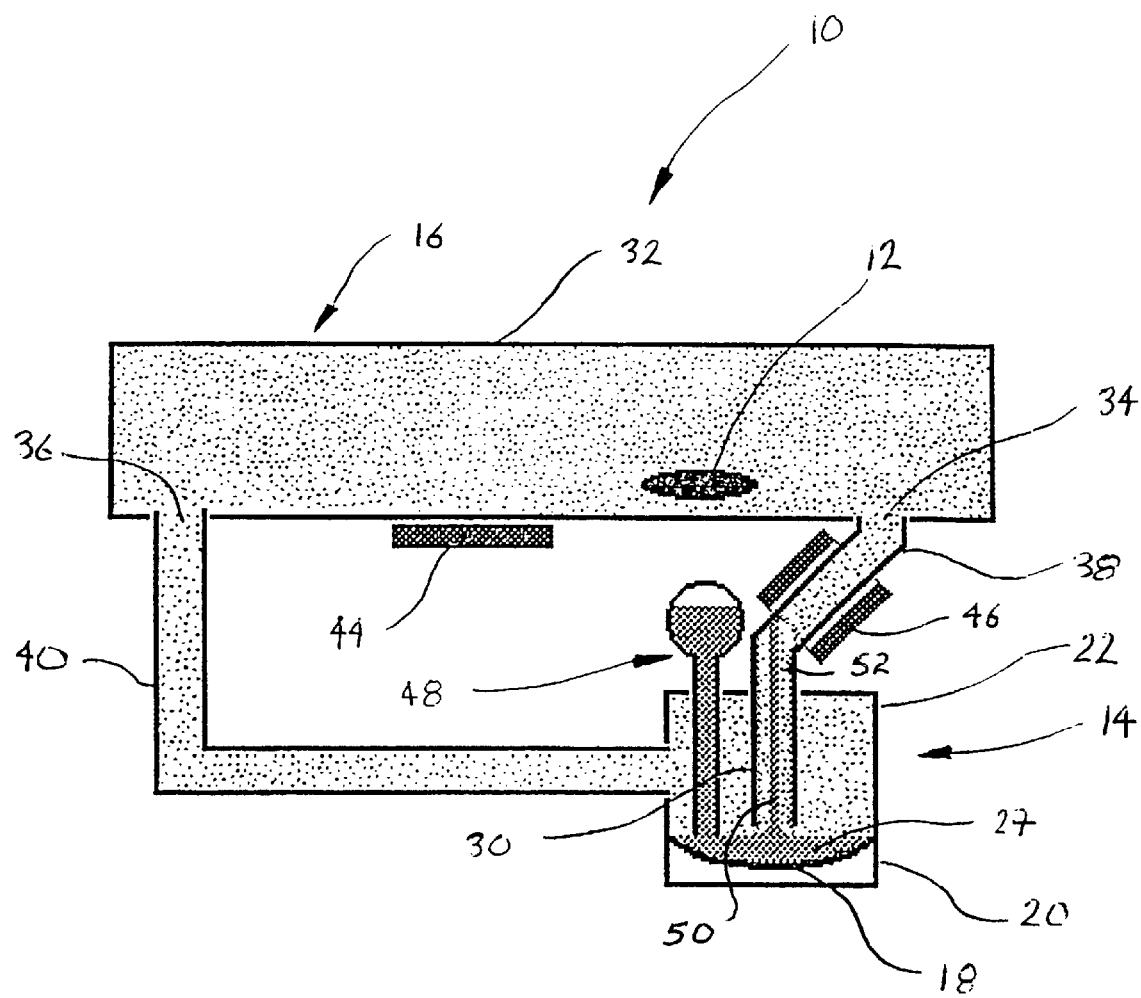
FIG. 3 is a schematic sectional view of a further embodiment of a sterilisation apparatus.

As shown in FIGS. 1 to 3 there are various embodiments of a sterilisation apparatus shown generally as 10 being designed to receive an article 12 requiring sterilisation. For ease of reference the same numerals are used to designate like or similar components of the various apparatus 10.

The sterilisation apparatus 10 comprises an aerosol generator 14 operatively coupled to a sterilisation chamber 16. In these embodiments the aerosol generator 14 includes an ultrasonic transducer 18 which is electrically coupled to an ultrasound generator (not shown). The remainder of the aerosol generator 14 is similar in construction to that described in the applicant's International patent publication No. WO 94/08727. The ultrasonic transducer 18 is mounted within a transducer housing 20 which can be any form but in this example is generally cylindrical in shape with a circular base. The transducer housing 20 is connected to a nebulisation chamber 22 which includes a conical-shaped partition ceiling 24 and a dish-shaped base 25 configured to hold a sterilisation agent 27 such as hydrogen peroxide, gluteraldegide or formaldegide etc. A liquid transfer media 29 such as water locates between the transducer 18 and the dish-shaped base 25. Thus, a nebulisation and expansion cavity 26 and 28 is located beneath and above, respectively, the ceiling 24. The nebulisation chamber 22 is also cylindrical with a dome-shaped roof. The nebulisation chamber 22 and/or the sterilisation chamber 16 may be of a disposable design.

Importantly the sterilisation apparatus 10 further includes a tube 30 which passes vertically through an apex of the partition ceiling 24. The tube 30 can have any cross-section but in this example is of a circular cross-section throughout its length with an inlet disposed coaxially within the nebulisation cavity 26 above the ultrasonic transducer 18. An outlet of the tube 30 is located within the expansion chamber 28. The ceiling 24 also includes one or more drainholes 31 located in its periphery.

The sterilisation chamber 16 includes a sterilisation container 32 which may be of any shape suitable for housing the article 12 to be sterilised. The container 32 includes an aerosol inlet 34 and an aerosol outlet 36 formed in its bottom wall. The aerosol inlet 34 is in fluid communication with the expansion cavity 28 via aerosol inlet conduit 38. The aerosol outlet 36 is in communication with the nebulisation cavity 26 via an aerosol outlet conduit 40. The inlet conduit 38 passes through the domed roof only of the nebulisation chamber 22 whereas the outlet conduit 40 passes through both the domed roof and the partition ceiling 24.

The sterilisation apparatus 10 of FIGS. 1 and 2 include additional features such as an air valve 42 mounted to the sterilisation container 32 being designed to permit pressurisation of the container 32. The sterilisation apparatus 10 of FIGS. 2 and 3 also includes:

(i) an additional ultrasonic transducer 44 operatively coupled to the sterilisation container 32;

(ii) a heater 46 in heat conductive communication with the inlet conduit 38; and (iii) a riser tube and tank assembly 48 located immediately above the sterilising agent 27 with the tank extending outside the expansion chamber 22.

The riser tube and tank assembly 48 maintains a constant level of sterilising agent during nebulisation so as to achieve an improved efficiency whereby the aerosol is generated within the tube 30. However, the sterilisation apparatus need not include the riser tube assembly.

It is the applicant's intention to construct the sterilisation chamber 16 and possibly the aerosol generator 14 as a disposable design. In this example the sterilisation container 32 will be constructed of a plastics material and releasably fits to the inlet and outlet conduits 38 and 40 as a socket-fit. In another example as illustrated in FIG. 3 the aerosol generator may be of a non-disposable design.

In operation sterilisation of the article 12 is effected by three general steps, namely:

(i) the sterilising agent is nebulised via activation of the transducer 18 whereby an aerosol of the sterilising agent is recirculated through the sterilisation chamber 16 and returned to the aerosol generator 14;

(ii) condensation or coagulation of the aerosol is promoted within the sterilisation chamber 16 by activation of the other ultrasonic transducer 44; and (iii) the sterilisation chamber 16 and article 12 are rinsed and dried by conventional techniques.

Condensation of the aerosol may also be promoted by locating a heater 46 about the inlet conduit 38 of the apparatus 10. This heater 46 is designed to heat the aerosol which encourages condensation of aerosol on or within the article 12. Alternatively or additionally the sterilisation chamber 16 may be pressurised via the air valve 42 to promote condensation of the aerosol.

As disclosed in International patent publication number WO 94/08727, which is included herein by way of reference, the ultrasonic transducer 18 produces a fountain 50 of the sterilizing agent within an inlet of the tube 30 where the aerosol 52 is produced. It is understood that the kinetic energy of the fountain 50 moving together with the aerosol 52 within the tube 30 increases the static pressure of the aerosol 52 within the tube 30 thereby inducing a pressure drop across the tube 30 which alone serves to propel the aerosol 52. The aerosol 52 is sucked through the tube 30 as the fountain 50 and aerosol 52 together move through the tube 30 like a "piston" so as to recirculate the aerosol 52 through the sterilization chamber 16. Any aerosol which condenses within the expansion cavity 28 or liquid which passes into the cavity 28 passes along the partition ceiling 24 and through the drainholes 31 into the nebulization chamber 26.

Additionally any sterilising agent not converting to an aerosol will return to the reservoir of sterilising agent, via the tube 30, within the nebulisation chamber 22.

Recirculation of the sterilizing agent in the aerosol form through the container 32 or sterilizing chamber 16 ensures that substantially full coverage and penetration of the article 12 with the aerosol 52 is achieved. In order to then obtain effective sterilization of the article 12 the aerosol 52 is condensed via the further ultrasonic transducer 44, the heater 46 and/or pressurization of the container 32 via the air valve 42. In each case the relatively cool article 12 promotes the condensation of aerosol for liquid disinfection or sterilization of the article 12. Advantageously sterilization of the article 12 is conducted at ambient temperature and pressure whereby condensation is made possible to promote sterilization of the article 12. The further ultrasonic transducer 44 can also be activated for presterilizing ultrasonic cleaning of the article 12.

It will be appreciated that damage to the transducer 18 can occur when the aerosol generator 14 is not filled or replenished with sterilising agent. Conventionally transducers such as piezoceramic transducers are protected from damage using temperature, capacitance or other sensors. These sensors are incorporated as an additional element and this involves extra cost.

It is recognised that the generation of aerosols is accompanied by cavitation which is a non-linear process. The spectrum of frequencies present during the cavitation do not exist in the fundamental voltage applied to a transducer. The frequency spectrum includes not only the fundamental frequency of generation but also noise of cavitation and subharmonics.

Figure 4:
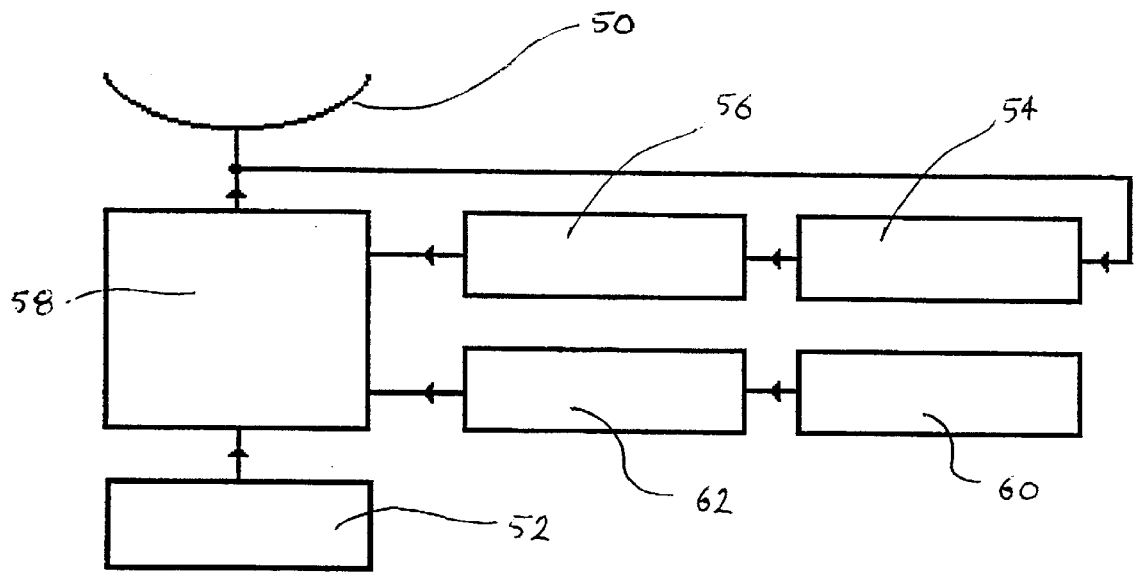
FIG. 4 is a diagrammatic representation of one embodiment of a switching device.

According to a further aspect of the present invention, an embodiment of which is illustrated in FIG. 4, a signal from a piezoceramic transducer 50 passes through a filter 54 and a detector 56 to a switch 58. The switch 58 controls the on-off operation of an ultrasonic generator 52. Cavitation of a liquid, such as a sterilising agent, via the transducer 50 will not be detected until shortly after it occurs. Therefore, the switch 58 must remain on for a brief initial period of operation. Therefore, a delay line 62 introduces this period of delay time so that a blocking signal generator 60 passes through the delay line 62 and turns the switch 58 off unless a signal is received from detector 56 indicating cavitation. The blocking signal from the generator 60 starts simultaneously with the voltage from the ultrasonic generator 52.

When liquid in the nebulisation chamber is present, cavitation occurs and the piezoceramic transducer 50 receives the cavitation signal. The signal is passed through the filter/filters 54 and the detector 56 to the switch 58. The switch 58 will not change the on state of the ultrasonic generator 52 and voltage is applied to the piezoceramic transducer 50. If liquid in the nebulisation chamber is not available, the signal of cavitation does not pass to the filter 54 and the switch 58 and hence the switch 58 turns off the ultrasonic generator 52 via the blocking signal.

In this embodiment the switching device comprises the filter 54, detector 56, switch 58, and delay line 62. It should be appreciated that the switching device may exclude specific components of this embodiment or include additional components depending on the application.

Now that preferred embodiments of the present invention have been described in some detail it will be apparent to those skilled in the art that the sterilisation apparatus, method of sterilisation, and switching device have at least the following advantages:

(i) effective sterilisation is produced by a combination of penetration of the aerosol together with condensation of the aerosol on the articles surface;

(ii) the consumption of sterilising agent in its aerosol form is relatively low;

(iii) the additional energy imparted to aerosol articles significantly increases the surface energy of the sterilising agent and its sterilising activity; and (iv) effective protection of the transducer can be achieved without requiring additional sensors.

Those skilled in the art will appreciate that the invention described herein is susceptible to variations and modifications other than those specifically described. For example, the sterilisation apparatus may include more than one aerosol generator. In this instance each of the aerosol generators may produce an aerosol form of different sterilising agents. These aerosols may be applied simultaneously or consecutively in a programmed sequence to the article to be sterilised. Due to the synergy between different sterilising agents the efficiency of the sterilisation process can be significantly increased.

Although it is preferred that nebulisation of the sterilising agent is achieved using an ultrasonic transducer, other means of nebulisation such as heating are within the ambit of the present invention. The invention is not restricted to hydrogen peroxide as a sterilising agent but rather extends to any liquid solution having sterilising properties. The transducer 18 itself, rather than the base of the nebulisation chamber, may be designed to contain the sterilisation agent. Air may be forced into the sterilisation container 32 to promote condensation of the aerosol or conversely air may be drawn from the container 32 to assist in drying of the article. Drying may also be effected by acoustical vibration. For example, this may be effected by the transducer where there is no sterilising agent present. An absorbent system may be included in a return line to the aerosol generator to absorb condensed aerosol. The aerosol may be electrically charged and controls by electro, magnetic or electromagnetic fields to enhance the efficiency of sterilisation.

The aerosol generator may be coupled to a breathing ventilation system which constitutes the sterilisation chamber. The breathing ventilation system may include a child's incubator, a ventilator, or an apparatus for treating sleep apnoea.

The switching device may detect the low level of any liquid within a reservoir and is not restricted to sterilising agents.

All such variations and modifications are to be considered within the scope of the present invention the nature of which is to be determined from the foregoing description.

The claims defining the invention are as follows:

1. A sterilization apparatus comprising:
    an aerosol generator being adapted to generate an aerosol of a sterilizing agent, the generator including an ultrasonic transducer being operatively coupled to or forming part of a reservoir which is adapted to contain the sterilizing agent, and a tube positioned adjacent the reservoir such that a fountain of the sterilizing agent as produced by the ultrasonic transducer spouts into the tube; and
    a sterilization chamber operatively coupled to the aerosol generator so as to receive a recirculatory flow of the aerosol, the kinetic energy of the fountain being effective in increasing the static pressure of the aerosol within the tube thereby inducing a pressure drop across the tube which alone is sufficient to propel the aerosol through the tube to produce the recirculatory flow, and the sterilization chamber being designed to receive an article requiring sterilization whereby in operation the recirculatory flow of the aerosol through the sterilization chamber is effective in sterilizing the article.

2. A sterilization apparatus as defined in claim 1 wherein the tube is positioned above the reservoir, the ultrasonic transducer being effective in producing the fountain of the sterilizing agent into an inlet of the tube where the aerosol is produced.

3. A sterilization apparatus as defined in claim 1 wherein the sterilization chamber includes an inlet and an outlet operatively coupled to the aerosol generator so as to provide the recirculatory flow of the aerosol through the sterilization chamber.

4. A sterilization apparatus as defined in claim 3 wherein an outlet of the tube is coupled to or defines the inlet of the sterilization chamber.

5. A sterilization apparatus as defined in claim 3 wherein the outlet of the sterilization chamber is coupled to or defines an air inlet, the aerosol being propelled through the tube under the assistance of air being drawn through the air inlet.

6. A sterilization apparatus as defined in claim 1 further including a partition ceiling located above the sterilizing agent, the ceiling including one or more drain holes which permit recycling of condensed aerosol or liquid sterilizing agent to the aerosol generator.

7. A sterilization apparatus as defined in claim 1 further comprising means for effecting condensation of the aerosol within or on the article.

8. A sterilization apparatus as defined in claim 7 wherein said means includes one or more of the following contrivances:
   i) a heating element operatively coupled to the inlet of the sterilization chamber;
   ii) an ultrasonic transducer operatively coupled to the sterilization chamber; and/or
   iii) a device for increasing the pressure of aerosol within the sterilization chamber.

9. A sterilization apparatus as defined in claim 1 also comprising means for rinsing and/or drying the condensed aerosol within or on the sterilization chamber together with the article.

10. A sterilization apparatus as defined in claim 1 wherein the aerosol generator and/or the sterilization chamber are disposable.

11. A method of sterilization comprising the steps of:
providing a sterilization apparatus including an aerosol generator and a sterilization chamber operatively coupled to each other, the generator including an ultrasonic transducer being operatively coupled to or forming part of a reservoir which is adapted to contain the sterilizing agent, and a tube positioned adjacent the reservoir such that a fountain of the sterilizing agent as produced by the ultrasonic transducer spouts the tube;
locating an article requiring sterilization in the sterilization chamber; and
providing a recirculatory flow of an aerosol of the sterilizing agent through the sterilization chamber, the kinetic energy of the fountain being effective in increasing the static pressure of the aerosol within the tube thereby inducing a pressure drop across the tube which alone is sufficient to propel the aerosol through the tube to produce the recirculatory flow whereby in operation the recirculatory flow of the aerosol through the sterilization chamber is effective in sterilizing the article.

12. A method of sterilization as defined in claim 11 further comprising the step of condensing the aerosol within or on the article.

13. A method of sterilization as defined in claim 12 additionally including the steps of rinsing the aerosol having been condensed within or on the article and thereafter drying the article.

14. A method of sterilization as defined in claim 13 wherein drying of the article involves activating an acoustical transducer whereby a flow of air passes through the sterilization chamber to effect drying of the article.

* * * * *

UNITED STATES PATENT AND TRADEMARK OFFICE
CERTIFICATE OF CORRECTION

PATENT NO.    : 6,379,616 B1
DATED         : April 30, 2002
INVENTOR(S)   : Sheiman It is certified that error appears in the above-identified patent and that said Letters Patent is hereby corrected as shown below:

<u>Title page,</u>
Item [73], change:
"Sheiman Ultrasonic Research (AU)" to -- Sheiman Ultrasonic Research Foundation Pty Ltd (AU) --.

Signed and Sealed this

Twelfth Day of November, 2002

Attest:

Attesting Officer

JAMES E. ROGAN
*Director of the United States Patent and Trademark Office*